(12) United States Patent
Hamas

(10) Patent No.: US 9,084,668 B2
(45) Date of Patent: Jul. 21, 2015

(54) PACKAGING FOR STERILE IMPLANT

(75) Inventor: Robert S. Hamas, Dallas, TX (US)

(73) Assignee: Ideal Implant Incorporated, Dallas, TX (US)

( * ) Notice: Subject to any disclaimer, the term of this patent is extended or adjusted under 35 U.S.C. 154(b) by 1404 days.

(21) Appl. No.: 12/325,693

(22) Filed: Dec. 1, 2008

(65) Prior Publication Data

US 2010/0133133 A1    Jun. 3, 2010

(51) Int. Cl.
| | |
|---|---|
| *A61B 17/06* | (2006.01) |
| *A61B 19/02* | (2006.01) |
| *A61L 15/00* | (2006.01) |
| *A61F 2/00* | (2006.01) |
| *A61F 2/12* | (2006.01) |

(52) U.S. Cl.
CPC *A61F 2/0095* (2013.01); *A61F 2/12* (2013.01)

(58) Field of Classification Search
CPC ........ A61F 2/0095; A61F 2/12; B65D 77/046
USPC ........ 206/438, 363, 828, 557, 656, 526, 63.3, 206/570, 493, 565, 588, 5.1, 210; 623/7, 8, 623/4.1–6.64; 220/23.87, 23.86, 23.83, 220/605, 606, 635
See application file for complete search history.

(56) References Cited

U.S. PATENT DOCUMENTS

| | | | | |
|---|---|---|---|---|
| 3,755,042 | A * | 8/1973 | Robertson et al. | 156/245 |
| 4,482,053 | A * | 11/1984 | Alpern et al. | 206/439 |
| 4,501,363 | A * | 2/1985 | Isbey, Jr. | 206/570 |
| 4,697,703 | A * | 10/1987 | Will | 206/438 |
| 4,750,619 | A | 6/1988 | Cohen et al. | |
| 5,354,337 | A * | 10/1994 | Hoy | 623/7 |
| 5,494,162 | A | 2/1996 | Treace et al. | |
| 5,664,695 | A * | 9/1997 | Young et al. | 215/375 |
| 5,669,501 | A | 9/1997 | Hissong et al. | |
| 5,868,253 | A * | 2/1999 | Krueger et al. | 206/438 |
| 6,050,398 | A * | 4/2000 | Wilde et al. | 206/5.1 |
| 6,622,864 | B1 * | 9/2003 | Debbs et al. | 206/438 |
| 2002/0033393 | A1 * | 3/2002 | Fux | 220/4.23 |
| 2007/0034538 | A1 * | 2/2007 | Landis | 206/438 |

* cited by examiner

*Primary Examiner* — Mickey Yu
*Assistant Examiner* — Chun Cheung
(74) *Attorney, Agent, or Firm* — The Webb Law Firm

(57) ABSTRACT

A sterile packaging system having an inner sterile dome-shaped tray and cover and an outer sterile-on-inside-only, bowl-shaped tray for accommodating the inner sterile dome-shaped tray and cover, the bowl-shaped tray having an annular rim and a cover over the annular rim, the outer bowl-shaped tray having at least two gripping surfaces extending from an outer surface.

8 Claims, 3 Drawing Sheets

PACKAGING FOR STERILE IMPLANT

BACKGROUND OF THE INVENTION

1. Field of the Invention

The present invention relates to packaging for the delivery of sterile implants, for example, mammary prostheses, in a manner to facilitate handling in the operating room.

2. Description of Related Art

Currently, packaging for sterile implants, and, in particular, mammary prostheses, involves an inner sterile tray and cover for containing the sterile implant and an outer tray and cover that are sterile on the inside and non-sterile on the outside. Together, the trays and prosthesis may be packaged in a non-sterile cardboard box. In the operating room, one nurse removes the trays from the cardboard box, carefully removes the cover from the outer tray without touching the inner tray, and inverts the outer tray to drop the sterile contents onto a sterile surface which may be the hands of a scrub nurse. Alternatively, one nurse holds the opened outer tray steady while a scrub nurse reaches in very carefully to avoid contaminating her hands to remove the sterile inner tray. The scrub nurse then removes the cover over the prosthesis making it available to the surgeon.

The trays in existing packaging systems tend to be made of flexible polycarbonate with a smooth surface that can be slippery. A precision grip of current outer trays is not easy and secure because the bottoms tend to be too large relative to the span of the hand of an average nurse and the sides slope away from the bottom. In addition, any indentations or projections on the bottom or sides of current outer trays are not of appropriate orientation and/or of sufficient length, for example, only ¼ to ⅜ inch, and/or of sufficient width relative to the long axis of the digits for the tips of the thumb and at least one finger to maintain a secure grip on the tray. This configuration often makes it necessary for a nurse to hold the outer tray with both hands for stability when presenting it to the scrub nurse to remove the inner tray. When inverting the outer tray to drop the sterile contents onto a sterile surface, the nurse often finds it necessary to hold the outer tray with both hands for stability and security so the tray does not slip and drop, contaminating the sterile surface. Also, existing packaging systems do not provide a configuration that allows the nurse to easily and securely grip the outer tray with one hand while removing the sealing cover with the other hand or to easily and securely grip the outer tray with one hand while inverting it to drop the sterile contents onto a sterile surface.

Attempts by the nurse to improve gripping on the outer tray of existing packaging systems by squeezing and deforming it to alter its configuration are limited by the close proximity of the underlying inner tray, compression against the inner tray that could make its removal more difficult, and possible shifting of the inner tray that could result in its contamination.

SUMMARY OF THE INVENTION

It is an object of this invention to provide a packaging system for packing a sterile object in an inner sterile container within an outer container sterile on the inside such that the outer configuration of the outer container provides for a secure grip of the outer container with one hand.

Briefly, according to one embodiment of this invention, there is provided a sterile packaging system for a generally dome-shaped prosthesis comprising an inner sterile dome-shaped tray for accommodating the generally dome-shaped prosthesis and having an opening with an annular rim extending away from the opening and having a cover extending over the annular rim, and an outer sterile-on-inside-only, bowl-shaped tray for accommodating the inner sterile dome-shaped tray and cover, the bowl-shaped tray having an annular rim and a cover extending over the annular rim. The outer bowl-shaped tray has at least two opposing gripping surfaces extending from the outer surface of the outer bowl-shaped tray that are generally parallel or converge toward the interior of the tray. The configuration of the opposing gripping surfaces is such that opposing gripping surfaces can be compressed by thumb and finger pressure to easily and securely hold and/or invert the outer bowl-shaped tray with one hand without altering the configuration of the tray.

Briefly, according to an alternate embodiment of this invention, there is provided a sterile packaging system for a generally dome-shaped prosthesis comprising an inner sterile dome-shaped tray for accommodating the generally dome-shape prosthesis and having an opening with an annular rim extending away from the opening and having a cover extending over the annular rim, and an outer sterile-on-inside-only, bowl-shaped tray for accommodating the inner sterile dome-shaped tray and cover, the bowl-shaped tray having an annular rim and a cover extending over the annular rim. The outer bowl-shaped tray has at least one handle-shaped gripping extension extending from the outer surface of the outer bowl-shaped tray, with two opposing gripping surfaces that are generally parallel or converge toward the interior of the tray. The area of each opposing gripping surface is at least one square inch. The gripping extensions extend from the opening of the outer bowl-shaped tray a distance to at least an imaginary plane parallel to the rim and extending through the surface of the bowl-shaped tray without cutting through the interior of the bowl-shaped tray. The gripping extension has gripping surfaces that are a generally triangular shape when viewed from the side with one edge thereof lying in the imaginary plane providing a stabilizing foot.

A precision grip is required for precise control of the position of the outer tray and involves grasping the gripping surfaces between the tips of the thumb and fingers, especially the index and middle fingers. For a precision grip, the configuration of opposing gripping surfaces for the tips of the thumb and at least one finger determines if the object can be held easily and securely.

For easy and secure precision gripping of the outer tray, it has been found that the configuration of the opposing gripping surfaces for the tips of the thumb and at least one finger should be greater than ¾ inch in length relative to the long axis of the digits, greater than ½ inch in width for one digit, and be generally parallel or converge toward the interior of the tray. In addition, precision gripping of the outer tray is enhanced by a configuration with sufficient area for gripping by two, three or four fingertips and for gripping by some portion of the palmar surfaces of the thumb and fingers in addition to their tips.

BRIEF DESCRIPTION OF THE DRAWINGS

Further features and other objects and advantages will become apparent from the following detailed description made with reference to the drawings in which.

DESCRIPTION OF THE PREFERRED EMBODIMENTS

Figure 1:
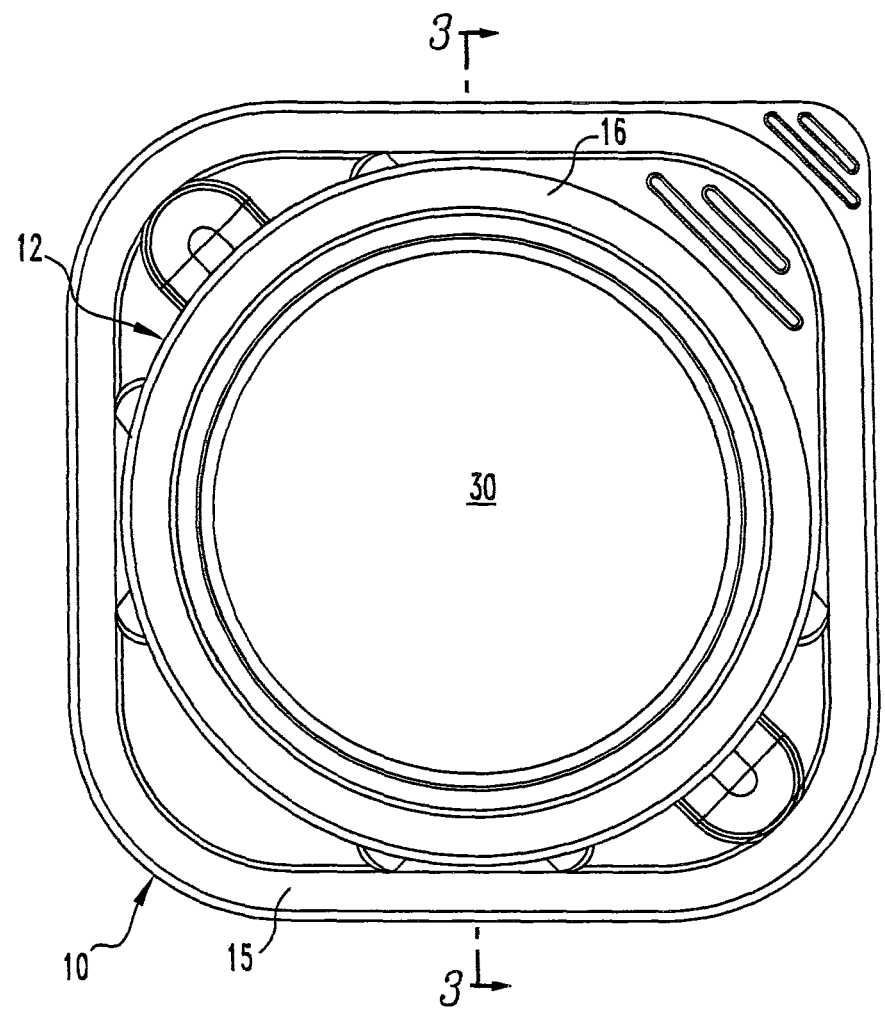
FIG. 1 is a top view of a packaging system, according to one embodiment of this invention, illustrating inner and outer trays without sealing covers in place and a prosthesis held in the inner tray.
Figure 2:
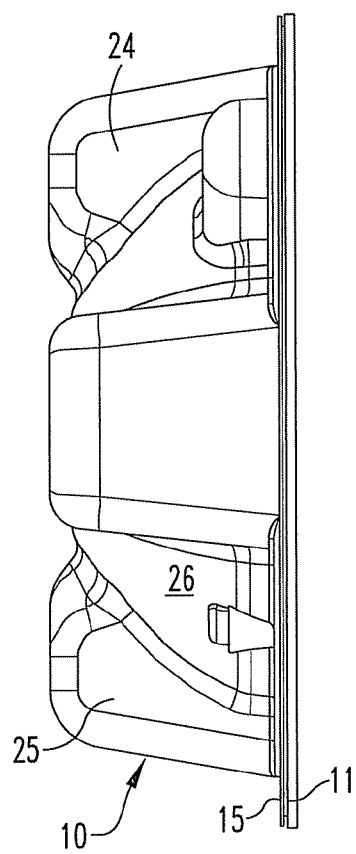
FIG. 2 is a side view of the packaging system shown in FIG. 1.
Figure 3:
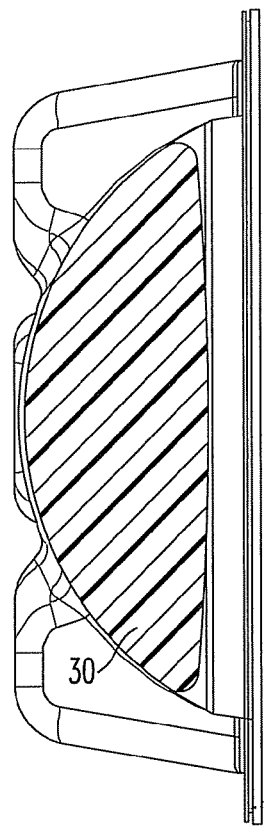
FIG. 3 is a section view of taken along lines 3-3 of FIG. 1.
Figure 5:
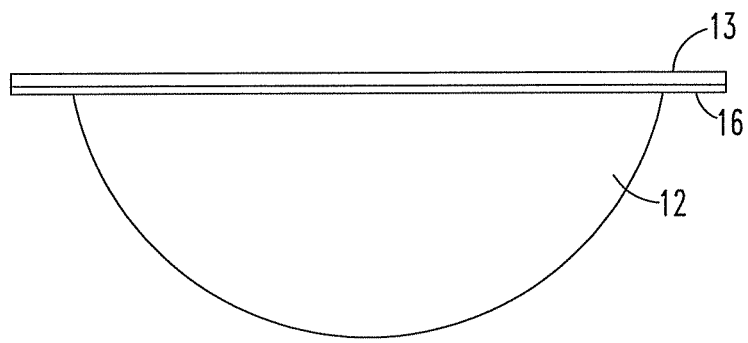
FIG. 5 is a stand-alone side view of an inner tray as shown in FIG. 1.

Referring now to the drawings, the packaging system illustrated comprises an outer tray 10. The outer tray 10 has an inverted dome for receiving an inner sterile tray 12. The outer tray has an opening with a rim 15 extending outward from the edge of the opening and lying substantially in a plane. The cover 11 overlies the rim 15 enabling sealing of the cover to the tray with an adhesive that will release the cover when the cover is peeled away. In a similar fashion, the inner tray has an opening with a rim 16 extending outward from the edge of the opening and lying substantially in a plane. The cover 13 overlies the rim 16 enabling sealing of the cover to the tray with an adhesive that will release the cover when the cover is peeled away. The cover 11 for the outer tray 10 is shown in FIGS. 2 and 3. The cover 13 for the inner sterile tray 12 is shown in FIG. 5. The implant 30 is shown resting in the inner tray (FIGS. 1 and 3.)

Figure 4:
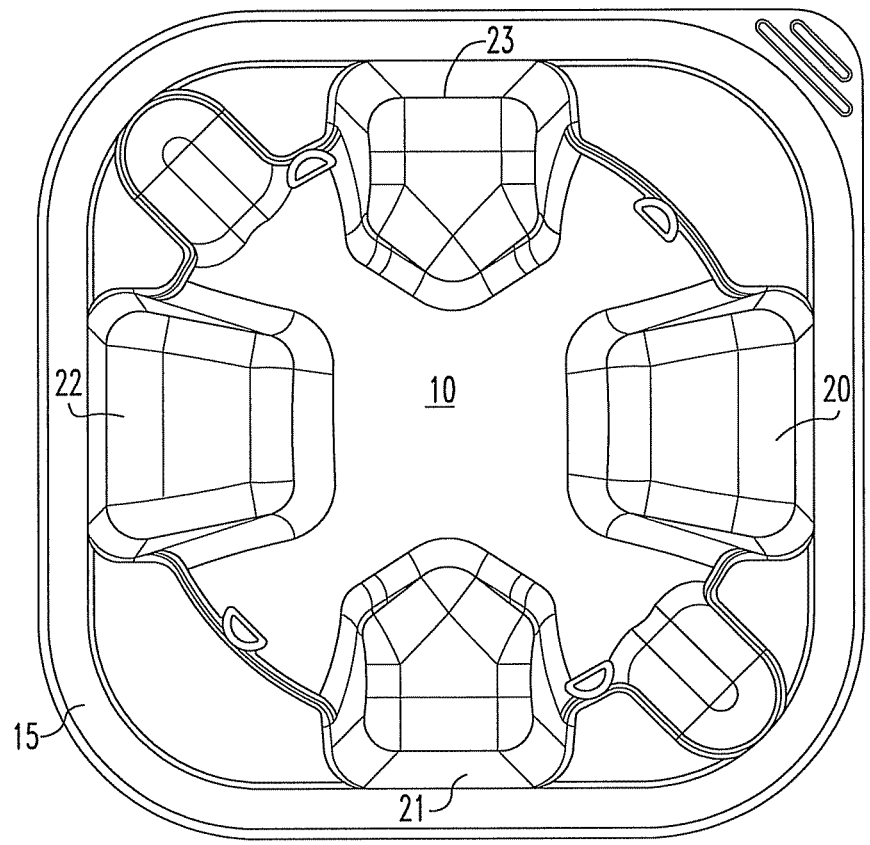
FIG. 4 is a top view of the empty outer tray as show in FIG. 1.

The outer tray is shaped to have four handle-shaped gripping extensions 20, 21, 22, 23 extending from the outer surface. The gripping extensions have opposing gripping surfaces 24, 25 extending outward from the outer surface 26 of the outer tray 10. In the embodiment illustrated, the gripping surfaces are spaced apart at the rim at least about 2 inches and each has a total area of about 1 square inch. This enables the easy and secure gripping of the two surfaces with the thumb and at least one finger of one hand. It is preferred that the opposing gripping surfaces be spaced apart between 1 and 3 inches at the rim, be greater than ¾ inch in length relative to the long axis of the digits, and greater than ½ inch in width for one digit. The gripping extensions all extend at least an equal distance away from the rim to an imaginary plane generally parallel to the rim and extending through the bowl-shaped surface of the outer tray, but not cutting through the interior of the tray. In this way, the gripping extensions can support the outer tray on a surface without tipping or rocking. Viewed from a side (see FIG. 2), the gripping surfaces of the gripping extensions have a somewhat triangular shape with the edge of the bowl comprising the hypotenuse. Viewed from the top (see FIG. 4), the gripping extensions 20 and 22 have two opposing gripping surfaces that converge toward the interior of the tray while gripping extensions 21 and 23 have two generally parallel gripping surfaces. The gripping extensions have a somewhat trapezoidal shape viewed from the top.

According to a preferred embodiment, the outer tray is clear polycarbonate approximately 0.04 inch thick and the rim is approximately 0.05 inch thick. The gripping extensions being hollow, thumb and finger pressure on the flexible gripping surfaces will move the gripping surfaces toward each other causing them to bow inward without compression against or shifting of the inner tray. This bowing of the gripping surfaces enables a better grip.

It is an advantage, according to this invention, that the outer bowl-shaped tray can be easily and securely held in one hand and inverted by gripping with the thumb and at least one finger on opposing gripping surfaces without altering the configuration of the tray.

Having thus defined my invention in the detail and particularity required by the Patent Laws, what is desired protected by Letters Patent is set forth in the following claims.

The invention claimed is:

1. A sterile packaging system for generally dome-shaped prostheses comprising:
   an inner sterile dome-shaped tray tier accommodating the generally dome-shaped prostheses and having an open base with an annular rim extending away from the open base of the dome, a cover extending over the annular rim;
   an outer sterile-on-inside-only, bowl-shaped tray for accommodating the inner sterile dome-shaped tray and cover, the outer bowl-shaped tray having an annular rim and a cover extending over the annular rim; and
   the outer bowl-shaped tray having at least one handle-shaped gripping extension with opposing gripping surfaces for the tips of the thumb and at least one finger extending from an outer surface of the outer bowl-shaped tray, the area of each opposing gripping surface being at least one square inch, being greater than ¾ inch in length relative to the long axis of the digits and being greater than ½ inch in width for one digit, said gripping surfaces extending from the outer bowl-shaped tray rim a distance at least to an imaginary plane parallel to the rim and extending through the surface of the bowl-shaped tray without cutting through the interior of the bowl-shaped tray, said gripping surfaces having a generally triangular shape with one edge thereof lying in said imaginary plane providing a stabilizing foot.

2. The packaging system according to claim 1, wherein at least two opposing gripping surfaces are generally parallel.

3. The packaging system according to claim 1, wherein at least two opposing gripping surfaces converge toward the interior of the tray.

4. The packaging system according to claim 1, wherein the opposing gripping surfaces are spaced apart at between 1 and 3 inches.

5. The packaging system according to claim 1, wherein the outer bowl-shaped tray is polycarbonate having a thickness of about 0.04 inch.

6. The packaging system according to claim 5, wherein the rim of the outer-bowl shaped tray has a thickness of about 0.05 inch.

7. The packaging system according to claim 1, wherein finger pressure will move the gripping surfaces causing them to bow.

8. A sterile packaging system for generally dome-shaped prostheses comprising:
   an inner sterile dome-shaped tray for accommodating the generally dome-shaped prostheses and having an opening with an annular rim extending away from the opening and a cover extending over the annular rim;
   an outer sterile-on-inside-only, bowl-shaped tray for accommodating the inner sterile dome-shaped tray and cover, the outer bowl-shaped tray having an annular rim and a cover extending over the annular rim; and
   the outer bowl-shaped tray having at least one handle-shaped gripping extension having at least two opposing gripping surfaces for the tips of the thumb and at least one finger extending from an outer surface of the outer bowl-shaped tray, the configuration of the gripping surfaces being such that when gripped by a thumb and at least one finger of one hand, the outer bowl-shaped tray can be held securely and inverted, the area of each opposing gripping surface being at least one square inch and being greater than ¾ inch in length relative to the long axis of the digits and being greater than ½ inch in width for one digit, wherein at least two opposing gripping surfaces converge toward the interior of the tray.

\* \* \* \* \*